US00PP30686P2

(12) United States Plant Patent
Flore

(10) Patent No.: US PP30,686 P2
(45) Date of Patent: Jul. 9, 2019

(54) ***PHALAENOPSIS* PLANT NAMED 'MI00901'**

(50) Latin Name: *Phalaenopsis hybrida*
Varietal Denomination: MI00901

(71) Applicant: Febe Flore, Lochristi (BE)

(72) Inventor: Febe Flore, Lochristi (BE)

(73) Assignee: Floreac N.V. div. Microflor, Lochristi (BE)

( * ) Notice: Subject to any disclaimer, the term of this patent is extended or adjusted under 35 U.S.C. 154(b) by 0 days.

(21) Appl. No.: 15/732,947

(22) Filed: Jan. 12, 2018

(51) Int. Cl.
*A01H 6/62* (2018.01)

(52) U.S. Cl.
USPC ..... Plt./311

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Phalaenopsis* plant named 'MI00901', characterized by its relatively compact and upright plant habit; moderately vigorous to vigorous growth habit; strong flowering stems; freely flowering habit with typically two racemes per plant, each inflorescence with numerous flowers; and concave white-colored flowers.

2 Drawing Sheets

Botanical designation: *Phalaenopsis hybrida.*
Cultivar denomination: 'MI00901'.

BACKGROUND OF THE INVENTION

The present invention relates to a new and distinct cultivar of *Phalaenopsis* plant, botanically known as *Phalaenopsis hybrida*, and hereinafter referred to by the name 'MI00901'.

The new *Phalaenopsis* plant is a product of a planned breeding program conducted by the Inventor in Lochristi, Belgium. The objective of the breeding program is to develop new freely flowering *Phalaenopsis* plants with good leaf shape and unique and attractive flower patterns and coloration.

The new *Phalaenopsis* plant originated from a cross-pollination in December, 2009 in Lochristi, Belgium of *Phalaenopsis hybrida* 'Ikaria', disclosed in U.S. Plant Pat. No. 19,778, as the female, or seed, parent with a proprietary selection of *Phalaenopsis hybrida* identified as code number PH01770, not patented, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in August, 2013.

Asexual reproduction of the new *Phalaenopsis* plant by in vitro meristem propagation in a controlled environment in Lochristi, Belgium since November, 2014 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MI00901'. These characteristics in combination distinguish 'MI00901' as a new and distinct *Phalaenopsis* plant:

1. Relatively compact and upright plant habit.
2. Moderately vigorous to vigorous growth habit.
3. Strong flowering stems.
4. Freely flowering habit with typically two racemes per plant, each inflorescence with numerous flowers.
5. Concave white-colored flowers.

Plants of the new *Phalaenopsis* can be compared to plants of the female parent, 'Ikaria'. Plants of the new *Phalaenopsis* differ primarily from plants of 'Ikaria' in the following characteristics:

1. Plants of the new *Phalaenopsis* are more compact than plants of 'Ikaria'.
2. Plants of the new *Phalaenopsis* are more freely flowering than plants of 'Ikaria'.

Plants of the new *Phalaenopsis* can be compared to plants of the male parent selection. Plants of the new *Phalaenopsis* differ primarily from plants of the male parent selection in the following characteristics:

1. Leaves of plants of the new *Phalaenopsis* are lighter and brighter green in color than leaves of plants of the male parent selection.
2. Flowers of plants of the new *Phalaenopsis* are concave whereas flowers of plants of the male parent selection are flat.

Plants of the new *Phalaenopsis* can be compared to plants of *Phalaenopsis hybrida* 'Dame Blanche', disclosed in U.S. Plant Pat. No. 24,346. In side-by-side comparisons, plants of the new *Phalaenopsis* differ primarily from plants of 'Dame Blanche' in flower shape as flowers of the new *Phalaenopsis* are concave whereas flowers of plants of 'Dame Blanche' are flat.

Plants of the new *Phalaenopsis* can also be compared to plants of *Phalaenopsis hybrida* 'MI00419', not patented. In side-by-side comparisons, plants of the new *Phalaenopsis* differ primarily from plants of 'MI00419' in the following characteristics:

1. Plants of the new *Phalaenopsis* have larger leaves than plants of 'MI00419'.
2. Plants of the new *Phalaenopsis* are more freely flowering than plants of 'MI00419'.
3. Flowers of plants of the new *Phalaenopsis* are broader than flowers of plants of 'MI00419'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet is a side perspective view of a typical flowering plant of 'MI00901' grown in a container.

The photograph on the second sheet is a close-up view of a typical flower of 'MI00901'.

DETAILED BOTANICAL DESCRIPTION

The aforementioned photographs and following observations and measurements describe plants grown during the autumn and early winter in 10-cm containers in a glass-covered greenhouse in Lochristi, Belgium and under cultural practices typically used in commercial *Phalaenopsis* production. During the production of the plants, day and night temperatures ranged from 18° C. to 29° C. and light levels ranged from 150 Watt/m$^2$ to 375 Watt/m$^2$. Plants were 76 weeks old when the photographs and description were taken. In the following description, color references are made to The Royal Horticultural Society Colour Chart, 2015 Edition, except where general terms of ordinary dictionary significance are used.

Botanical classification: *Phalaenopsis hybrida* 'MI00901'.

Parentage:

*Female parent.*—*Phalaenopsis hybrida* 'Ikaria', disclosed in U.S. Plant Pat. No. 19,778.

*Male parent.*—Proprietary selection of *Phalaenopsis hybrida* identified as code number PH01770, not patented.

Propagation:

*Type.*—By in vitro meristem propagation.

*Time to initiate roots, summer.*—About nine to ten weeks at temperatures about 26° C.

*Time to initiate roots, winter.*—About ten to eleven weeks at temperatures about 26° C.

*Time to produce a rooted young plant, summer.*—About 140 to 160 days at temperatures about 26° C.

*Time to produce a rooted young plant, winter.*—About 150 to 180 days at temperatures about 26° C.

*Root description.*—Thick, fleshy; typically grey green in color, towards the apex, close to light green; actual color of the roots is dependent on substrate composition, water quality, fertilizer, substrate temperature and age of roots.

*Rooting habit.*—Low to non-branching; sparse.

Plant description:

*Plant form and growth habit.*—Herbaceous epiphyte; upright plant habit with typically two branched racemes per plant, each inflorescence with numerous flowers; monopodial; moderately vigorous to vigorous growth habit and moderate growth rate.

*Plant height, substrate level to top of foliar plane.*—About 18 cm.

*Plant height, substrate level to top of inflorescences.*—About 46.9 cm.

*Plant diameter or spread.*—About 31.3 cm.

Leaf description:

*Arrangement and quantity.*—Distichous, simple; sessile; about eight per plant.

*Length.*—About 18.3 cm.

*Width.*—About 7.8 cm.

*Aspect.*—Mostly flat to slightly arching.

*Shape.*—Obovate; slightly carinate.

*Apex.*—Broadly acute, unequal.

*Base.*—Sheathing.

*Margin.*—Entire; slightly revolute to non-revolute.

*Texture and luster, upper and lower surfaces.*—Slightly furrowed, glabrous; slightly glossy.

*Venation pattern.*—Camptodromous.

*Color.*—Developing leaves, upper surface: Close to 137B. Developing leaves, lower surface: Close to between 144A and 146B. Fully expanded leaves, upper surface: Close to NN137C; venation, close to NN137C. Fully expanded leaves, lower surface: Close to 144A; towards the margins, close to between 147A and 147B; venation, close to between 143C.

Inflorescence description:

*Appearance and flowering habit.*—Showy zygomorphic flowers arranged on axillary branched racemes; typically three racemes per plant; each inflorescence with about 14 flowers; flowers face outwardly on arching inflorescences supported by upright peduncles; flowers with three petals, two lateral petals and one center petal transformed into a labellum and three sepals.

*Fragrance.*—None detected.

*Time to flower.*—Plants begin flowering about 18 weeks after an inductive cooling period.

*Flower longevity.*—Long flowering period, individual flowers maintain good substance for about five months on the plant; flowers not persistent.

*Inflorescence length (lowermost flower to inflorescence apex).*—About 26.9 cm.

*Inflorescence width.*—About 19.7 cm.

*Flower buds.*—Height: About 1.9 cm. Diameter: About 1.4 cm. Shape: Broadly ovate. Color: Close to N144D; towards the base, close to between 145B and 145C.

*Flower diameter.*—About 8.1 cm by 12.5 cm.

*Flower depth.*—About 3.8 cm.

*Petals, quantity and arrangement.*—Three, two lateral petals and one center petal transformed into a labellum.

*Lateral petals.*—Length: About 4.5 cm. Width: About 6 cm. Shape: Reniform; slightly to moderately concave. Apex: Rounded. Margin: Entire. Texture and luster, upper and lower surfaces: Smooth, glabrous, velvety; matte. Color: When opening, upper surface: Close to NN155D. When opening, lower surface: Close to lighter than 150D; towards the margins and apex, close to NN155D. Fully opened, upper and lower surfaces: Close to lighter than NN155D.

*Labellum*.—Appearance: Tri-lobed with two lateral lobes and a central lobe. Length, lateral lobe: About 2.3 cm. Width, lateral lobes: About 1.5 cm. Length, central lobe: About 3.4 cm. Width, central lobe: About 2.3 cm. Shape, lateral lobes: Obovate. Shape, central lobe: Roughly rhomboidal to deltoid. Apex, lateral lobes: Obtuse. Apex, central lobe: Cleft with two moderately long narrow recurved cirrose tips. Margins, lateral lobes: Entire, undulate. Margins, central lobe: Entire. Texture and luster, upper and lower surfaces: Smooth, glabrous, velvety; matte. Callosities: Located at the base of the labellum and attachment point of the lateral petals; about 5 mm in length, about 6 mm in width and about 5 mm in height. Color: When opening, upper surface: Lateral lobes: Close to NN155D; stripes towards the base, close to 60B to 60C; basal margins, close to 2B. Central lobe: Close to NN155C; towards the base, close to 1B; stripes towards the base, close to 60B; basal margins, close to 60B; cirrose apices, close to 4D. Callosities: Close to 8A; stripes, close to 60B. When opening, lower surface: Lateral lobes: Close to NN155D; basal margins, close to 2B. Central lobe: Close to 155A; towards the base, close to 1B; basal margins, close to 60B; cirrose apices, close to 4D. Fully opened, upper surface: Lateral lobes: Close to NN155D; stripes towards the base, close to 60C; basal margins, close to 5A. Central lobe: Close to NN155C; towards the base, close to 1A; stripes towards the base, close to 60B; basal margins, close to 60B; cirrose apices, close to 4D. Callosities: Close to 8A; stripes, close to 60B. Fully opened, lower surface: Lateral lobes: Close to NN155D; basal margins, close to 5A. Central lobe: Close to 155A; towards the base, close to 2A to 2B; basal margins, close to 60B; cirrose apices, close to 4D.

*Sepals*.—Quantity and arrangement: Three, two lower lateral sepals and one upper dorsal sepal. Length, lateral sepal: About 4.7 cm. Width, lateral sepals: About 3 cm. Length, dorsal sepal: About 4.6 cm. Width, dorsal sepal: About 3.5 cm. Shape, lateral sepals: Ovate; moderately concave. Shape, dorsal sepal: Obovate; moderately concave. Apex, lateral and dorsal sepals: Obtuse. Base, lateral and dorsal sepals: Truncate. Margin, lateral and dorsal sepals: Entire. Texture and luster, lateral and dorsal sepals, upper and lower surfaces: Smooth, glabrous, velvety; matte. Color, lateral sepals: When opening, upper surface: Close to 150D to lighter than 150D; towards the margins and base, close to 157D; fine dots towards the base, close to 64B. When opening, lower surface: Close to 145C; towards the margins and apex, close to 145D and between 145D and 150D. Fully opened, upper surface: Close to 157B; towards the margins and apex, close to NN155D; fine dots towards the base, close to 64B to 64C. Fully opened, lower surface: Close to 145C to 145D; towards the margins and apex, close to NN155D; main vein, close to 182B. Color, dorsal sepal: When opening, upper surface: Close to NN155C. When opening, lower surface: Close to 145C; towards the margins and apex, close to between 150D and 157D. Fully opened, upper surface: Close to NN155D. Fully opened, lower surface: Close to 157D; towards the margins and apex, close to NN155D to lighter than NN155D.

*Peduncles*.—Length: About 50.8 cm. Diameter: About 5.5 mm. Strength: Very strong. Aspect: Upright to about 50° from vertical. Texture and luster: Smooth, glabrous; matte. Color: Close to N200A with fine dots, close to 148C.

*Pedicels*.—Length: About 3.9 cm. Diameter: About 3.5 mm. Strength: Moderately strong. Aspect: About 75° from peduncle axis. Texture and luster: Smooth, glabrous; matte. Color: Close to 147C; proximally, close to 147A.

*Reproductive organs*.—Androecium: Column length: About 8 mm. Column width: About 6 mm. Column color: Close to NN155D. Pollinia quantity: Two. Pollinia diameter (per two pollinia): About 2 mm. Pollinia color: Close to 23A. Gynoecium: Stigma length: About 3 mm. Stigma width: About 4 mm. Stigma shape: Reniform. Stigma color: Close to NN155C. Ovary length: About 8 mm. Ovary diameter: About 1.5 mm. Ovary color: Close to lighter than 145C. Seeds and fruits: Seed and fruit development have not been observed on plants of the new *Phalaenopsis* to date.

Pathogen & pest resistance: Plants of the new *Phalaenopsis* have not been shown to be resistant to pathogens and pests common to *Phalaenopsis* plants.

Temperature tolerance: Plants of the new *Phalaenopsis* have been observed to tolerate high temperatures of about 40° C. and suitable for USDA Hardiness Zone 10.

It is claimed:

1. A new and distinct *Phalaenopsis* plant named 'MI00901' as illustrated and described.

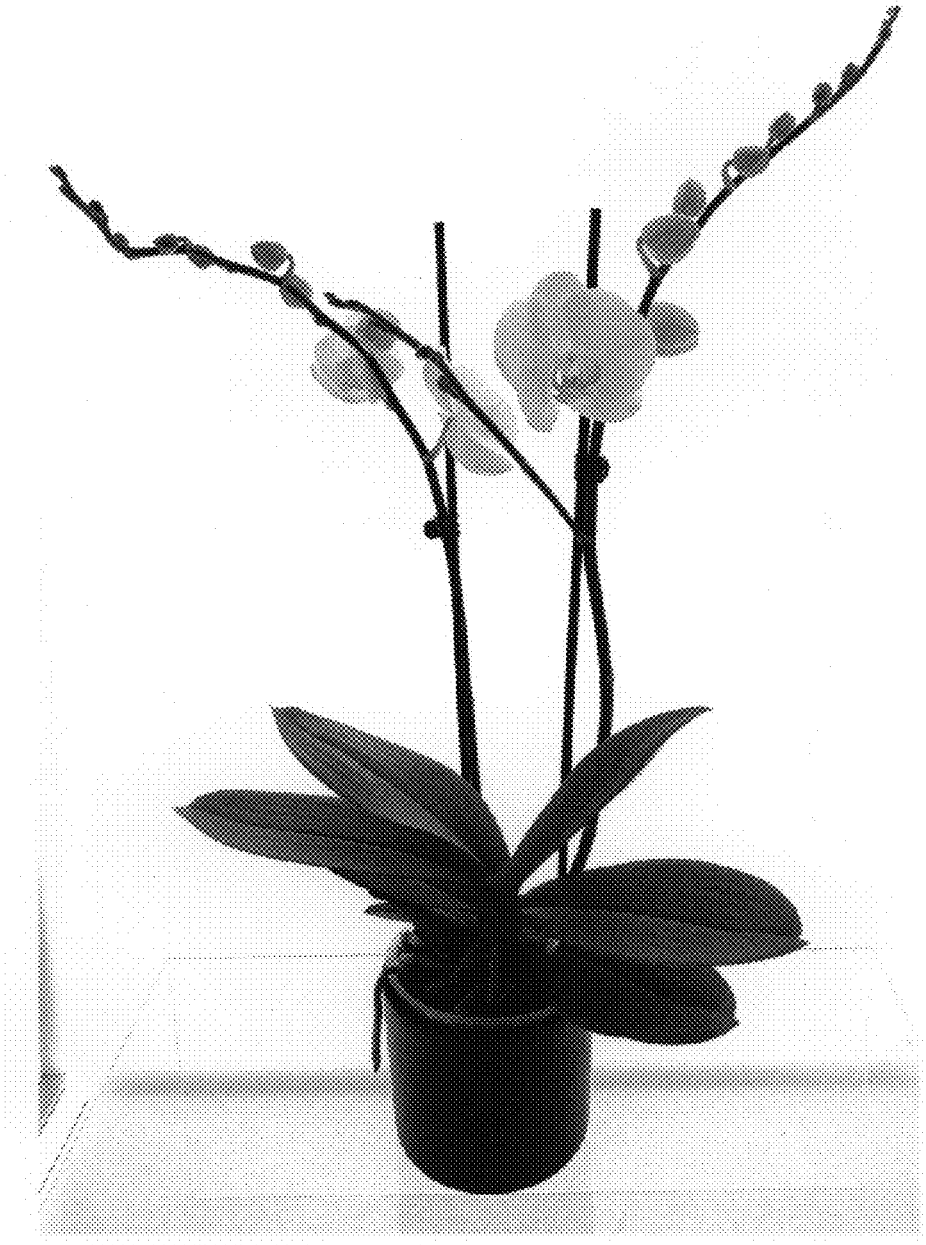

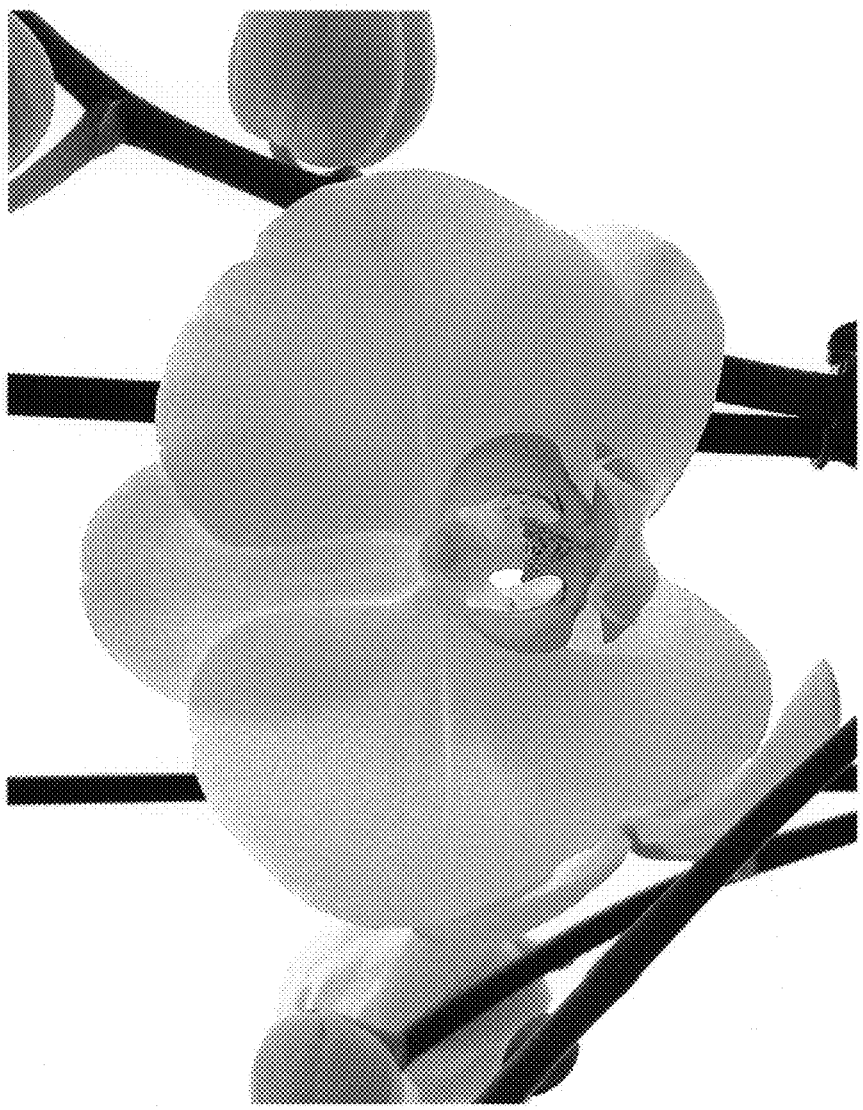

* * * * *